United States Patent [19]

Picciolo et al.

[11] 3,971,703

[45] July 27, 1976

[54] METHOD OF DETECTING AND COUNTING BACTERIA

[75] Inventors: Grace L. Picciolo, Tantallon; Emmett W. Chappelle, Baltimore, both of Md.

[73] Assignee: The United States of America as represented by the Administrator of the National Aeronautics and Space Administration, Washington, D.C.

[22] Filed: Mar. 5, 1975

[21] Appl. No.: 555,641

Related U.S. Application Data

[63] Continuation-in-part of Ser. No. 475,337, May 31, 1974, abandoned.

[52] U.S. Cl. ........................................... 195/103.5 R
[51] Int. Cl.² .......................................... C12K 1/00
[58] Field of Search ............................. 195/103.5 R

[56] References Cited
UNITED STATES PATENTS 3,616,253   10/1971   D'Eustachio................. 195/103.5 R
3,745,090   7/1973   Chappelle et al............ 195/103.5 R

*Primary Examiner*—Alvin E. Tanenholtz
*Attorney, Agent, or Firm*—Ronald F. Sandler; Gary F. Grafel; John R. Manning

[57] ABSTRACT

An improved method is provided for determining bacterial levels, especially in samples of aqueous physiological fluids, which method depends on the quantitative determination of bacterial adenosine triphosphate (ATP) in the presence of non-bacterial ATP. The bacterial ATP is released by cell rupture and is measured by an enzymatic bioluminescent assay. A concentration technique is included to make the method more sensitive. It is particularly useful where the fluid to be measured contains an unknown or low bacteria count.

19 Claims, No Drawings

3,971,703

METHOD OF DETECTING AND COUNTING BACTERIA

ORIGIN OF THE INVENTION

The invention described herein was made by employees of the United States Government and may be manufactured and used by or for the Government for governmental purposes without the payment of any royalties thereon or therefor.

This is a continuation-in-part of a prior copending application, Ser. No. 475,337, filed May 31, 1974 and now abandoned.

FIELD OF THE INVENTION

This invention relates to a method for detecting and counting the bacteria present, especially in aqueous physiological fluids. More particularly, this invention relates to an improved method for counting bacteria which depends on the presence and determination of adenosine triphosphate (ATP), which is nucleotide present in all known living matter.

BACKGROUND OF THE INVENTION

Procedures for rapid and routine quantitative detection and counting of bacteria are important, for instance, in the practice of medicine, where bacteria counts are required for such physiological fluids as blood and urine. The prior art includes classical techniques for growing bacteria, but these are slow and require complex media. For instance, methods presently used for determining and counting bacteria in urine are culture methods which include the streak and pour plat methods and the direct methods which include microscopic counting and an additional method which depends upon the ability of organisms to oxidize nitrites to nitrates. These methods have their disadvantages. Those methods depending on a culture can be questioned because the growth of a particular bacteria will vary significantly with the particular nutrient and other environmental factors. Moreover, a significant amount of time is required for growth to occur. The direct counting methods have the disadvantage of requiring highly skilled personnel.

The prior art now includes the method disclosed in U.S. Pat. No. 3,745,090, incorporated herein by reference, entitled "Method of Detecting and Counting Bacteria in Body Fluids". The method disclosed is both rapid and routine in nature. The method depends on the fact that there is some ATP within all known living matter, including bacteria. In order to determine the bacteria count in a given urine sample, for example, a nonionic detergent is added to the urine sample to rupture all of the non-bacteria cells, placing the ATP from such cells in soluble free form. The non-bacterial ATP can then be destroyed by adding an enzyme (ATPase), such as apyrase, that will hydrolyze free ATP. The apyrase is destroyed and the bacterial cells are ruptured at the same time, freeing their ATP, by adding a strong inorganic acid such as nitric acid. The resultant suspension contains free bacterial ATP and the acid. The acid is then neutralized with a buffer or diluted with distilled water. For the purpose of the remaining test, therefore, the only effective element in the suspension is the bacterial ATP.

A luciferase-luciferin mixture is prepared in soluble form with a buffering agent to compensate for the acid in the bacterial ATP suspension if the buffer had not been previously added to the suspension, so that the effectiveness of the luciferase is not overcome. A small quantity of magnesium chloride is added. The luciferase is an enzyme which catalyzes the reaction of luciferin with ATP in the presence of $Mg^{++}$, which light emission being one of the reaction end products. Luciferin is ia light emitting long chain thiol derivation.

One part of the bacterial ATP-acid solution is then mixed with one part of the luciferase-luciferin mixture. Bioluminescence will occur as a result of the reaction of the ATP with the luciferase, luciferin and the divalent metal ions. The resulting mixture is then brought into the presence of a photomultiplier system where the maximum light intensity of the bioluminescence is measured. The maximum intensity of the bioluminescence is related to the amount of ATP present which is, in turn, related to the amount of bacteria present in the original sample. A detailed description of the light measuring apparatus and techniques can be found in U.S. Pat. No. 3,756,920, issuing from a copending continuation-in-part application of U.S. Pat. No. 3,745,090 entitled "Automatic Instrument for Chemical Processing to Detect Micro-organisms in Biological Samples by Measuring Light Reactions", the disclosure of which is also incorporated by reference.

If the luciferase-luciferin mixture is present in excess the intensity of light produced is approximately proportional to the quantity of ATP present for the normal range to ATP concentrations.

OBJECTS OF THE INVENTION

Accordingly, it is an object of the present invention to provide an improved, more sensitive method for detecting and counting bacteria which substantially prevents or alleviates one or more of the disadvantages of the prior art.

Another object is to provide an improved, more sensitive method for detecting and counting bacteria utilizing a bioluminescent reaction of bacterial ATP when the sample to be analyzed also contains non-bacterial sources of ATP.

A further object is to provide an improved, more sensitive method for detecting and counting bacteria which yields more accurate results than methods of the prior art when samples contain low bacteria counts.

Another object is to provide an improved more sensitive method for detecting and counting bacteria in physiological fluid samples utilizing the high specificity of an enyzmatic reaction, which method is also capable of adaption to automatic equipment, thereby lessening the expenditure of time and obviating the necessity of requiring the use of experienced personnel.

These and other objects of the present invention will become apparent with reference to the following summary of the invention and the description of the preferred embodiments thereof.

SUMMARY OF THE INVENTION

According to the present invention, an improved, more sensitive method is provided for detecting and counting bacteria, especially in physiological fluids such as urine, which method is especially valuable where the sample contains a relatively high level of material which would interfere with a luciferase enzyme reaction. This method includes first rupturing the various non-bacterial cells containing ATP, by addition of a non-ionic detergent, without affecting the bacterial cells which also contain ATP, putting the ATP from such cells in soluble free form. The sample is then concentrated by centrifuging whereby the bacteria and any other particulate matter are separated from the supernatant phase containing almost all of the soluble ATP from the non-bacterial cells. An alternate procedure is to concentrate by centrifuging prior to the first step of rupturing the non-bacterial cells. The non-bacterial ATP is next destroyed by the addition of apyrase which hydrolyzes the free ATP. The pH level of the solution is then lowered by adding a suitable buffer to obtain a pH where the ATP from non-bacterial cells still left binding on large molecules and particulate matter is minimal. The resultant suspension is again centrifuged to reconcentrate the bacteria. The remaining steps in the method are identical to the prior art method disclosed in the aformentioned U.S. Pat. No. 3,745,090. The apyrase is destroyed and the bacterial cells are ruptured, freeing their ATP, by the addition of a strong inorganic acid such as nitric acid, leaving a solution of free bacterial ATP and the acid. The pH of the acid suspension is usually adjusted by use of a suitable buffer and the suspension is sometimes diluted, preferably with distilled water. A luciferase-luciferin mixture is prepared in soluble form with a buffering agent to compensate for the acid in the bacterial ATP solution if the buffering agent is not added to the suspension. A small quantity of magnesium chloride is added. One part of the bacterial ATP-acid solution is then mixed with one part of the luciferase-luciferin mixture. The resulting bioluminescence is measured by a photomultiplier system. This method is particularly useful where the fluid to be measured contains an unknown or low bacteria count.

DESCRIPTION OF THE INVENTION

Basically, the object of the present method is to use a measurement of bacterial ATP as an indication of the number of bacteria present and, in order to do so, the interfering non-bacterial ATP must first be removed. The first step is to rupture the various non-bacterial cells containing ATP by the addition of a non-ionic detergent which does not affect the bacterial cells which also contain ATP. This places the ATP from the non-bacterial cells in soluble free form. In urine specimens the non-bacterial cells include such cells as erythrocytes, leucocytes, and epithelial cells. The detergent of choice for use with these non-bacterial cells present is TRITON X-100 (octyl phenoxy polyethoxyethanol). Other possible detergents used are within the class of surfactants as well as any other agents which will lyse cell membranes but not rupture bacterial cell walls. Organic solvents in various concentrations have been used.

It should be clearly understood that much of the present disclosure relates to measuring bacteria present in urine. Urine has bacterial cells containing bacterial ATP, soluble ATP, bound ATP, (i.e. bound to particulate and large molecule matter), and non-bacterial (mammalian) cells containing non-bacterial ATP. Food similarly has the same constituents except that its non-bacterial cells would not necessarily be mammalian. However, a pure bacterial culture would be expected to contain bacterial cells containing bacterial ATP, soluble ATP and bound ATP but no non-bacterial cells. In such a case there would be no requirement for the addition of a detergent, in this case, TRITON X-100, because there are no non-bacterial cells required to be ruptured.

After the non-ionic detergent is added to the urine sample, rupturing of the non-bacterial cells is generally carried out at ambient temperature and pressure, the sample sometimes being allowed to stand for from 1 minute to 1 hour, preferably from 5 to 20 minutes, the optimum being about 10 minutes. The optimum time the sample is allowed to stand after the non-ionic detergent is added is partially dependent upon the temperature since the rate of rupture will be increased appreciably for each degree of increase in temperature. Allowing the sample to stand for a long period of time or at elevated temperatures is to be avoided since, under either of those conditions, the non-ionic detergent might begin to attack the bacteria, thereby reducing the accuracy of the results obtained. An alternative is to allow centrifugation, the next step, for a long enough time. After vortexing, the sample is then concentrated by centrifuging, filtration, the addition of hydrophobic gels or lyophyzation, whereby the bacteria and other particulate matter such as membrane remnants from the aforementioned tissue cells and crystals from the urine are separated from the supernatant phase containing the soluble constituents of the urine. The supernatant phase includes almost all the soluble ATP from the non-bacterial cells but not the particulate bound non-bacterial ATP. An alternate method would be to concentrate by centrifuging prior to the first step of rupturing the non-bacterial cells. Nevertheless, the better practice is believed to be centrifugation after the cell rupturing because this process requires less apyrase. Centrifuging is advantageous because it concentrates the bacteria thereby improving sensitivity and also because, it allows removal of almost all the inhibitors present in the original sample. Typically, a 10 ml sample is used for the assay of ATP.

The non-bacterial ATP is next destroyed by the addition of apyrase which hydrolyzes the free soluble ATP still present in the pellet. The apyrase is 100% effective on free non-bound ATP. The apyrase required must be sufficient to destroy one $\mu$ mole of ATP in approximately 15 minutes.

A small amount of a saline solution is added to the apyrase-pellet solution in the centrifuge tube in order that any material that might be adhering to the walls of the tube will be washed down. Normally, about 5 ml is used. If more than that was added more of the apyrase solution would have to be added.

The next problem is to destroy the particulate bound ATP in the pellet. In order to accomplish this, the pH level of the solution is lowered by adding a suitable buffer to lower the pH to a point where ATP left binding on large molecules and particulate matter is minimal. In practice the lowest pH compatible with adequate apyrase activity is 4.25. A representative buffer for this application is sodium malate (Na malate). Other suitable buffers would be those with a pK covering a range of pH 4 to pH 5 such as glycine, glycyl glycine and lactic acid. The necessary concentration would be one which will maintain the pH between 4 and 4.5 in the presence of the chemical agents present in the sample. The concentration must also be such that it will not raise the pH of the subsequent bacterial extracting acid above pH 2. As the particulate bound ATP is released by the Na malate, the apyrase present will destroy it. The resultant suspension is again centrifuged to reconcentrate the bacteria.

The apyrase must then be destroyed and the bacterial cells ruptured to free their ATP. This is done by the addition of a strong inorganic acid such as nitric acid leaving a solution of free bacterial ATP and the acid. Other suitable acids would include perchloric acid, trichloroacetic acid and sulphuric acid or any inorganic acid that is highly ionized. The necessary concentrations are dependent on the type of the acid and the type of bacteria cells to be ruptured. For nitric acid a final concentration of between 0.1 and 0.15 N is adequate for all bacteria types that have been tested which include those bacterial species found in urine. The suspension will now contain the extracting acid, free bacterial ATP, bacterial ghosts and ghosts from the non-bacterial cells. The ghosts from the bacterial and non-bacterial cells have been found to be non-interfering with respect to the desired reaction.

At this point in the process three possible alternatives exist. A minimal quantity of sterile, deionized water may be added to the suspension to reduce the acidity so that a minimal quantity of buffer will be required to neutralize the acidity of the suspension to the pH optimal for the luciferase reaction. However, a volume of water which will raise the pH above the point where the apyrase is inactive is to be avoided. Another alternative embodiment may be used when the apyrase is permanently inactivated by the nitric acid ($HNO_3$) treatment. This situation usually occurs when the quantity of residual apyrase is small such as when a concentration technique is used whereby the bulk of the apyrase is discarded prior to the addition of $HNO_3$. As the buffering capacity of the tris-hydroxymethyl-aminomethane (TRIS) in which the luciferase is dissolved does not have to be great because of the pre-neutralization of the $HNO_3$ the luciferase may be dissolved in a lower TRIS concentration at a pH of 7.75. A third alternative is that if no water is added, the acidity of the resulting suspension must be neutralized by a buffer added to the suspension prior to mixing with luciferase, or, as an alternative, the luciferase must be prepared with enough buffer to compensate for the acidity of the suspension. The buffer commonly used, again, is TRIS. It is most often mixed with the luciferase-luciferin mixture. Other suitable buffers include phosphate and arsenate buffers or others with a pK of approximately 7. The desired effect is to maintain an optimal pH for luciferase activity (7.75) when the suspension is finally mixed with the luciferase-luciferin mixture. The amount of buffer added is dependent on the acid concentration of the sample. At this point in the process, after the buffer is added, the only effective element in the suspension is the bacterial ATP.

The luciferase-luciferin mixture used is prepared in soluble form with a small quantity of magnesium sulphate. Typically, 1 to 5 mg of partially purified luciferase per ml is mixed with 0.01 to 1.0 mg of luciferin per ml along with about 1.3 mg per ml of magnesium sulphate. Actually, any soluble magnesium salt can be used as the objective is to make the solution 0.01 M in $Mg^{--}$. In fact, other divalent metallic ions such as manganese can be used but heavy metals should be avoided. This solution should be at least 0.05 M in a buffer with a pK of approximately 7 at a pH of 7.75 where no buffer was added to the acidic suspension. Where buffer is added to the acidic suspension the molarity and pH should be such so that when the suspension is added to the luciferase-luciferin solution the final pH should be 7.75. It should be understood that whenever a luciferase-luciferin solution is referred to, it includes a soluble magnesium salt. For purposes of stabilization, this solution is lyophilized. The luciferase-luciferin is available commercially in this form. It is readied for use by adding water. The quantity of water added will depend on the activity desired. It should, because of its present high cost, be dissolved to a great extent when intended for application not requiring great sensitivity. An example of an average high volume would be dissolve 100 mg in 5 ml of water. A typical low volume for high sensitivity would call for about 75 mg in 1.5 ml of water.

At this point, a measured quantity, for example, 0.1 ml of the luciferase-luciferin solution is placed in a small transparent container. This container is placed in a light-tight reaction chamber adjacent to a photomultiplier tube without yet being light coupled to the tube. The container is rotated until it faces the cathode surface of the tube.

Now, the ATP is ready to be mixed with the solution in the container. Typically, a syringe is used to take up a 0.1 ml sample of the ATP solution. The syringe is then used to pierce a soft rubber septum on top of the container now facing the cathode surface of the photomultiplier tube. The syringe contents are then injected into the container. In this example a 1 to 1 volume relationship exists between the ATP solution and the luciferase-luciferin solution, but in fact, a 1 to 100 relationship, in either direction, could be used.

Upon injection, within 0.5 second, maximum intensity is achieved, the maximum being generally directly proportional to the amount of ATP present. However, at relative high ATP concentrations, the relationship between ATP and maximum light intensity is no longer linear and tends to level off. This is because of two factors, insufficient luciferase-luciferin and saturation of the photomultiplier tube or amplifier.

If we now take our peak light reading and have avoided saturation the quantity of ATP present can be determined from the light reading. Again, the light output will be directly proportional to the amount of ATP present. The photomultiplier output is calibrated with a standard unit of ATP. The output of the sample being measured is then compared with the light output of the standard unit. For example, 0.0001 mg of ATP would give you a reading of 5000 arbitrary light units. If the sample gave 2500 arbitrary light units we would calculate that the sample contained .00005 mg of ATP.

The object is now to determine the amount of bacteria present in a given sample. It should be recognized that a different amount of ATP is present in various types of species of bacteria, thus one has to calculate the amount of ATP per cell for each species. However, since variations are relatively small, approximation by averaging can be used. On the average it has been determined that there is about $1 \times 10^{-9}$ $\mu$gm of ATP per cell. From the example given above where the sample contained 0.00005 mg of ATP by dividing by the figure $1 \times 10^{-9}$ $\mu$gm ATP/cell, the result is that the sample contains $5 \times 10^7$ bacterial cells per ml.

The invention is further illustrated by the following example in which all parts and percentages are by weight unless otherwise indicated. This example is illustrative of results obtained with one embodiment of the invention and are provided to teach those skilled in the art how to practice the invention and to represent one mode contemplated for carrying out the invention.

EXAMPLE

Introduction

The example involves a procedure for obtaining the amount of bacteria present in a urine sample. The first part of this procedure involves rupturing the non-bacterial cells with a non-ionic detergent to free their ATP and then destroying that ATP as well as any free soluable ATP originally present.

a. A 10 ml urine sample was mixed with 0.2 ml of a 6% by volume Triton X-100 solution.

b. The sample was vortexed well.

c. The sample as then centrifuged at ambient pressure for 15 minutes at 20°C at 10,400 RCF × G and then decanted, thereafter, inverted on filter paper for a period of 5 minutes; a pellet remains.

d. 1.0 ml of a solution of 10 mg apyrase/ml 0.03 M $CaCl_2$ was added to the pellet.

e. The sample was then vortexed well.

f. The sample was then mixed well with 5.0 ml of a 0.9% saline solution and the sample allowed to stand for 15 minutes.

g. The sample was then mixed with 1.0 ml of a solution of 0.25 M Na malate—0.005 M sodium arsenate having a pH of 4.25.

h. The sample was again centrifuged at 10,400 RCF × G for 15 minutes at 20°C and the decant, thereafter, inserted on filter paper.

i. The sample was then mixed with 0.2 ml of 0.1 N $HNO_3$ and, thereafter, vortexed well and allowed to stand for 5 minutes.

j. The sample was then mixed with 0.2 ml of sterile, deionized $H_2O$.

k. The sample was vortexed well.

l. A syringe was used to extract 0.1 ml of the sample which was then injected through the septum of a container facing the cathode of a photomultiplier tube. The container contains 0.1 ml of a luciferase-luciferin solution which is 0.01 M in $MgSO_4$ and 0.2 M Tris, at a pH of 8.25.

m. A reading was then taken from the photometer of $2 \times 10^8$ light units where a standard ATP sample containing $1 \times 10^{-2}$ $\mu gm/ml$ was used to establish a base calibration of the photometer at a reading of $2 \times 10^7$ light units.

n. The sample under examination was calculated to have an ATP concentration of $1 \times 10^{-1}$ $\mu gm/ml$ which, using the average figure of $1 \times 10^{-9}$ $\mu gm/ATP/cell$ it is calculated that the sample had about $1 \times 10^8$ bacterial cells per ml.

The method of the instant invention, as disclosed herein, results in an improved, more sensitive method for detecting and counting bacteria. It can be conducted by non-microbiologists, freeing more highly skilled personnel for more effective use. The test is suitable for all bacteria; it is effective for aerobes and anaerobes; and it is generally unaffected by the presence of bacteriostatic agents which inhibit growth.

The method is not only suitable for use in analyzing urine samples to determine urinary tract infections by measuring the level of bacteria, but is is also adaptable to the determination of bacterial levels in other aqueous physiological fluids such as lymph fluid, plasma, blood, spinal fluid, saliva, and mucus, to name only a few, as well as bacteria removed from such a fluid. Further, it is particularly applicable to measuring bacterial levels in aqueous physiological fluids which have, in addition to the bacteria, both free soluble ATP and non-bacterial cells containing ATP.

The principles, preferred embodiments, and modes of operation of the present invention have been described in the foregoing specification. The invention which is intended to be protected herein, however, is not be construed as limited to the particular forms disclosed since these are to be regarded as illustrative rather than restrictive. Variations and changes may be made by those skilled in the art without departing from the spirit of the present invention.

What is claimed is:

1. A method of detecting and counting bacteria in a sample which contains bacterial cells and non-bacterial adenosine triphosphate comprising treating said sample by:
   a. removing soluble and non-bacterial adenosine triphosphate;
   b. desorbing bound adenosine triphosphate, the desorbed adenosine triphosphate also being removed;
   c. rupturing bacterial cells, thereby releasing bacterial adenosine triphosphate;
   d. adding a portion of the treated sample to a luciferase-luciferin solution; and
   e. measuring the emitted light level.

2. The method of claim 1 wherein the desorbing of bound adenosine triphosphate is carried out through lowering the pH of the sample.

3. The method of claim 2 wherein the pH is lowered by adding sodium malate.

4. The method of claim 3 wherein the sodium malate lowers pH to a level of between 4 and 4.5.

5. The method of claim 1, wherein the sample has its bacterial cells ruptured using an acid and thereafter has the hydrogen ion concentration of the acid treated sample lowered.

6. The method of claim 5 wherein the desorbing of bound adenosine triphosphate is carried out through lowering the pH of the sample.

7. The method of claim 6 wherein the pH is lowered by adding sodium malate.

8. The method of claim 7 wherein the sodium malate lowers the pH to a level of between 4 and 4.5.

9. A method of detecting and counting bacteria in a sample comprising treating said sample by:
   a. rupturing bacterial cells using an acid, thereby releasing bacterial adenosine triphosphate;
   b. lowering the hydrogen ion concentration of the acid treated sample by the addition of sterile, deionized water
   c. adding a portion of the treated sample to a luciferase-luciferin solution; and
   d. measuring the emitted light level.

10. The method of claim 9 wherein prior to rupturing the bacterial cells bound adenosine triphosphate are desorbed and removed.

11. The method of claim 10 wherein the desorbing of bound adenosine triphosphate is carried out through lowering the pH of the sample.

12. The method of claim 11 wherein the pH is lowered by adding sodium malate.

13. The method of claim 12 wherein the sodium malate lowers the pH to a level of between 4 and 4.5.

14. A method of detecting and counting bacteria in a fluid sample which contains bacterial and non-bacterial cells containing adenosine triphosphate comprising:

a. concentrating the non-soluble material in the fluid sample by removing the suspending fluid by filtration;
b. treating said sample by rupturing the non-bacterial cells with the addition of octyl phenoxy polyethoxyethanol to release adenosine triphosphate present in the non-bacterial cells without rupturing the bacterial cells;
c. hydrolyzing non-bacterial adenosine triphosphate with the addition of apyrase;
d. desorbing bound adenosine triphosphate by lowering the pH to between 4 and 4.5 with the addition of sodium malate, the desorbed adenosine triphosphate also being hydrolyzed;
e. removing the hydrolyzing agent and rupturing the bacterial cells with the addition of nitric acid, thereby releasing adenosine triphosphate;
f. reducing the hydrogen ion concentration by adding sterile, deionized water;
g. adding a portion of the treated sample to a luciferase-luciferin solution, and
h. measuring the emitted light level.

15. A method of detecting and counting bacteria comprising:

a. treating a solution containing bacterial cells and non-bacterial ATP by the addition of an ATP-ase;
b. reducing the amount of the ATP-ase present by a concentration technique to a level where the remaining ATP-ase can be kept inactive;
c. rupturing the bacterial cells;
d. reducing the acidity of the rupturing agent to a pH that will not allow reactivation of the ATP-ase by the addition of a diluent;
e. adding a portion of the treated sample to a luciferase-luciferin solution containing a bufferin; and
f. measuring the emitted light level.

16. The method of claim 15 wherein the ATP-ase is apyrase.

17. The method of claim 15 wherein the rupturing agent is nitric acid.

18. The method of claim 15 wherein the acidity of the rupturing agent is reduced by the addition of sterile, deionized water.

19. The method of claim 15 wherein the ATP-ase is apyrase, the rupturing agent is nitric acid and the acidity of the rupturing agent is reduced by the addition of sterile deionized water.

* * * * *